(12) United States Patent
Cowley

(10) Patent No.: US 12,023,065 B2
(45) Date of Patent: Jul. 2, 2024

(54) BI-STABLE SPRING-LATCH CONNECTOR FOR ULTRASONIC SURGICAL INSTRUMENTS

(71) Applicant: Covidien LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 883 days.

(21) Appl. No.: 16/999,215

(22) Filed: Aug. 21, 2020

(65) Prior Publication Data

US 2021/0059705 A1 Mar. 4, 2021

Related U.S. Application Data

(60) Provisional application No. 62/895,108, filed on Sep. 3, 2019.

(51) Int. Cl.
*A61B 17/32* (2006.01)
*A61B 17/00* (2006.01)

(52) U.S. Cl.
CPC ........... *A61B 17/320068* (2013.01); *A61B 17/00234* (2013.01); *A61B 2017/00477* (2013.01); *A61B 2017/320074* (2017.08)

(58) Field of Classification Search
CPC ...... A61B 17/320068; A61B 17/00234; A61B 17/32; A61B 2017/320074; A61B 2017/00477; F16L 37/107; F16L 37/113; F16L 37/248; F16L 37/252
See application file for complete search history.

(56) References Cited

U.S. PATENT DOCUMENTS

| | | |
|---|---|---|
| 1,813,902 A | 7/1931 | Bovie |
| 2,235,274 A | 3/1941 | Trehern |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |

(Continued)

*Primary Examiner* — Erich G Herbermann
(74) *Attorney, Agent, or Firm* — Carter, DeLuca & Farrell LLP

(57) ABSTRACT

A waveguide configured for use with an ultrasonic instrument includes a horn which engages an ultrasonic transducer to receive ultrasonic energy. A body distally extends from the horn in order to receive ultrasonic energy from the horn. A blade is fixedly engaged to a distal end of the body, and distally extends from the distal end of the body in order to receive ultrasonic energy from the body for treating tissue in contact with the blade. A bi-stable spring-latch connector releasably couples, under compression, the horn and the body, or the body and the blade.

18 Claims, 9 Drawing Sheets

(56) References Cited

U.S. PATENT DOCUMENTS

| | | |
|---|---|---|
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,836,897 A | 11/1998 | Sakurai et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Vanna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,241,312 B2 | 8/2012 | Messerly |
| 8,435,258 B2 | 5/2013 | Young et al. |
| 8,672,959 B2 | 3/2014 | Witt et al. |
| 2001/0048855 A1 | 12/2001 | Lin |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |

(56) References Cited

U.S. PATENT DOCUMENTS

| | | |
|---|---|---|
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2010/0298743 A1 | 11/2010 | Nield et al. |
| 2012/0078278 A1 | 3/2012 | Bales, Jr. et al. |
| 2012/0116263 A1 | 5/2012 | Houser et al. |
| 2013/0085419 A1 | 4/2013 | Stoddard et al. |
| 2013/0325047 A1* | 12/2013 | Craig ............ A61B 17/320092 606/169 |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2015/0323128 A1* | 11/2015 | Garvey .................. F16B 2/246 248/200.1 |
| 2017/0290583 A1* | 10/2017 | Reed ................ A61B 17/07207 |
| 2018/0360486 A1* | 12/2018 | Beaupre ......... A61B 17/320068 |

\* cited by examiner

BI-STABLE SPRING-LATCH CONNECTOR FOR ULTRASONIC SURGICAL INSTRUMENTS

CROSS-REFERENCE TO RELATED APPLICATIONS

This application claims the benefit of and priority to U.S. Provisional Patent Application Ser. No. 62/895,108 filed Sep. 3, 2019, the entire disclosure of which is incorporated by reference herein.

BACKGROUND

Technical Field

The present disclosure relates to ultrasonic surgical instruments and, more particularly, to a bi-stable spring-latch connector for ultrasonic surgical instruments.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Corded ultrasonic instruments operate in similar fashion except that, rather than having the generator and power source mounted on the handheld instrument itself, the handheld instrument is configured to connect to a standalone power supply and/or generator via a corded connection.

Regardless of the particular type and/or configuration of ultrasonic surgical instrument utilized, proper engagement between the horn and waveguide body, as well as the waveguide body and blade, ensures that the ultrasonic energy is properly transmitted to the end effector for treating tissue therewith.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

Provided in accordance with aspects of the present disclosure is a waveguide configured for use with an ultrasonic surgical instrument. The waveguide includes a horn configured to receive ultrasonic energy from an ultrasonic transducer, a body extending distally from the horn and configured to transmit the ultrasonic energy therealong, a blade extending distally from the body and configured to apply the ultrasonic energy to tissue in contact therewith to treat the tissue, and a bi-stable spring-latch connector releasably coupling, under compression, the horn and the body.

In an aspect of the present disclosure, the bi-stable spring-latch connector includes a female end disposed on a distal end of the horn and a male end disposed on a proximal end of the body. The female end may be configured to receive the male end thereby releasably coupling, under compression, the horn and the body.

In another aspect of the present disclosure, the female end of the bi-stable spring-latch connector may include an open-ended cylinder with a hollow cylindrical interior and a pair of grooves defining a double helix.

In still another aspect of the present disclosure, the male end of the bi-stable spring-latch connector is a cylindrical block including a pair of protrusions disposed on opposite sides of the cylindrical block and extending radially outwardly therefrom.

In yet another aspect of the present disclosure, the pair of protrusions disposed on the male end is configured to be rotated through the double helix of the female end.

In still yet another aspect of the present disclosure, closed ends of the double helix are perpendicular to a longitudinal axis defined through the female end, thereby maintaining the coupling, under compression, of the female end and the male end.

In another aspect of the present disclosure, the double helix is wound clockwise such that clockwise rotation of the male end relative to the female end couples the horn and the body.

In an aspect of the present disclosure, the double helix is wound counterclockwise such that counterclockwise rotation of the male end relative to the female end decouples the horn and the body.

In still another aspect of the present disclosure, the bi-stable spring-latch connector includes a male end disposed on a distal end of the horn and a female end disposed on a proximal end of the body. The female end may be configured to receive the male end thereby releasably coupling, under compression, the horn and the body.

Provided in accordance with aspects of the present disclosure is a waveguide configured for use with an ultrasonic surgical instrument. The waveguide includes a horn configured to receive ultrasonic energy from an ultrasonic transducer, a body extending distally from the horn and configured to transmit the ultrasonic energy therealong, a blade extending distally from the body and configured to apply the ultrasonic energy to tissue in contact therewith to treat the tissue, and a bi-stable spring-latch connector releasably coupling, under compression, the body and the blade.

In an aspect of the present disclosure, the bi-stable spring-latch connector includes a female end disposed on a distal end of the horn and a male end disposed on a proximal end of the body. The female end may be configured to receive the male end thereby releasably coupling, under compression, the body and the blade.

In another aspect of the present disclosure, the female end of the bi-stable spring-latch connector may include an open-ended cylinder with a hollow cylindrical interior and a pair of grooves defining a double helix.

In still another aspect of the present disclosure, the male end of the bi-stable spring-latch connector is a cylindrical block having a pair of protrusions disposed on opposite sides of the cylindrical block and extending radially outwardly therefrom.

In yet another aspect of the present disclosure, the pair of protrusions disposed on the male end is configured to be rotated through the double helix of the female end.

In still yet another aspect of the present disclosure, closed ends of the double helix are perpendicular to a longitudinal axis defined through the female end, thereby maintaining the coupling, under compression, of the female end and the male end.

In another aspect of the present disclosure, the double helix is wound clockwise such that clockwise rotation of the male end relative to the female end couples the body and the blade.

In an aspect of the present disclosure, the double helix is wound counterclockwise such that counterclockwise rotation of the male end relative to the female end decouples the body and the blade.

In still another aspect of the present disclosure, the bi-stable spring-latch connector includes a male end disposed on a distal end of the body and a female end disposed on a proximal end of the blade. The female end may be configured to receive the male end, thereby releasably coupling, under compression, the body and the blade.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
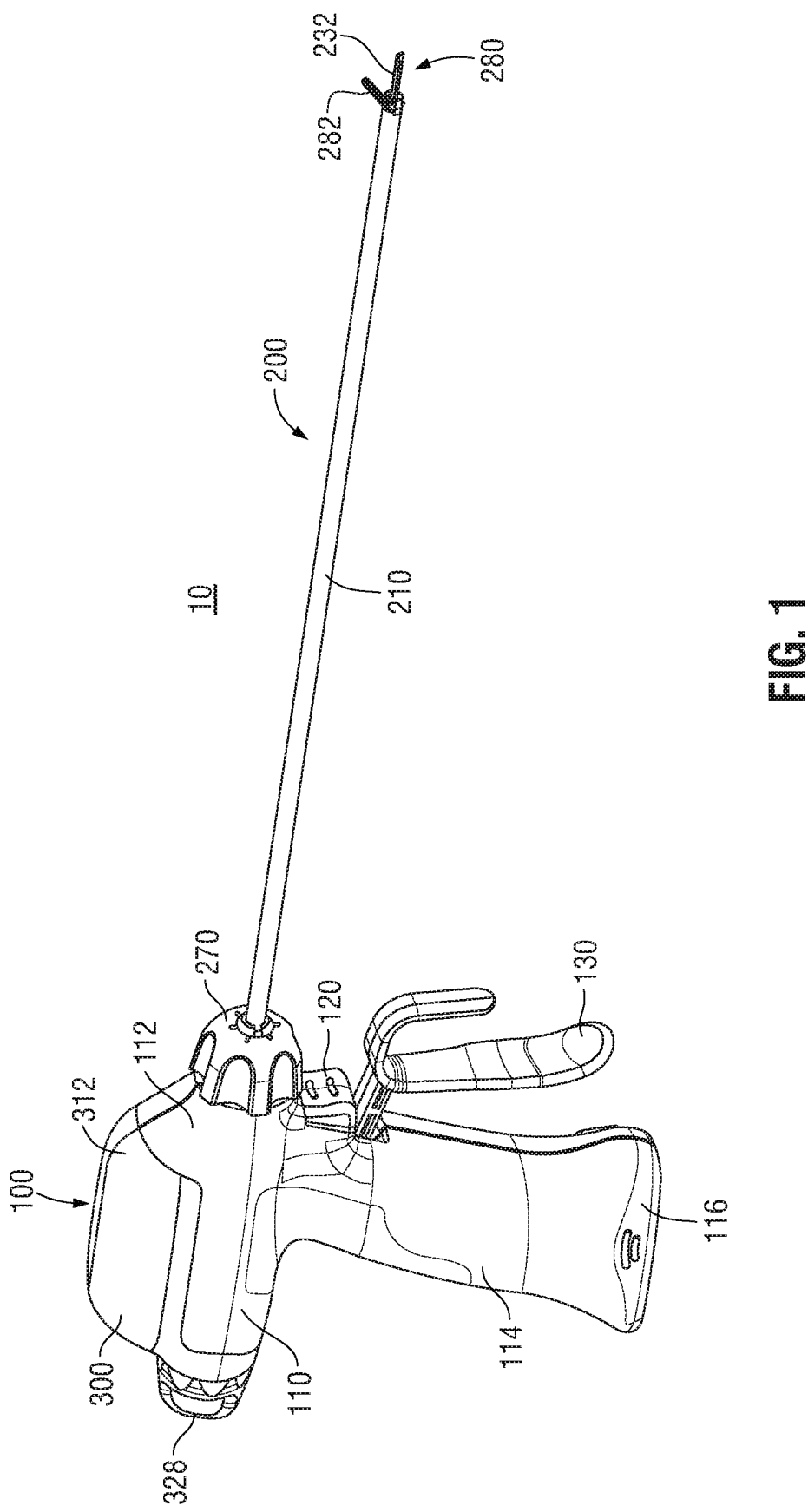
FIG. 1 is a perspective view of an ultrasonic surgical instrument provided in accordance with the present disclosure.
Figure 2:
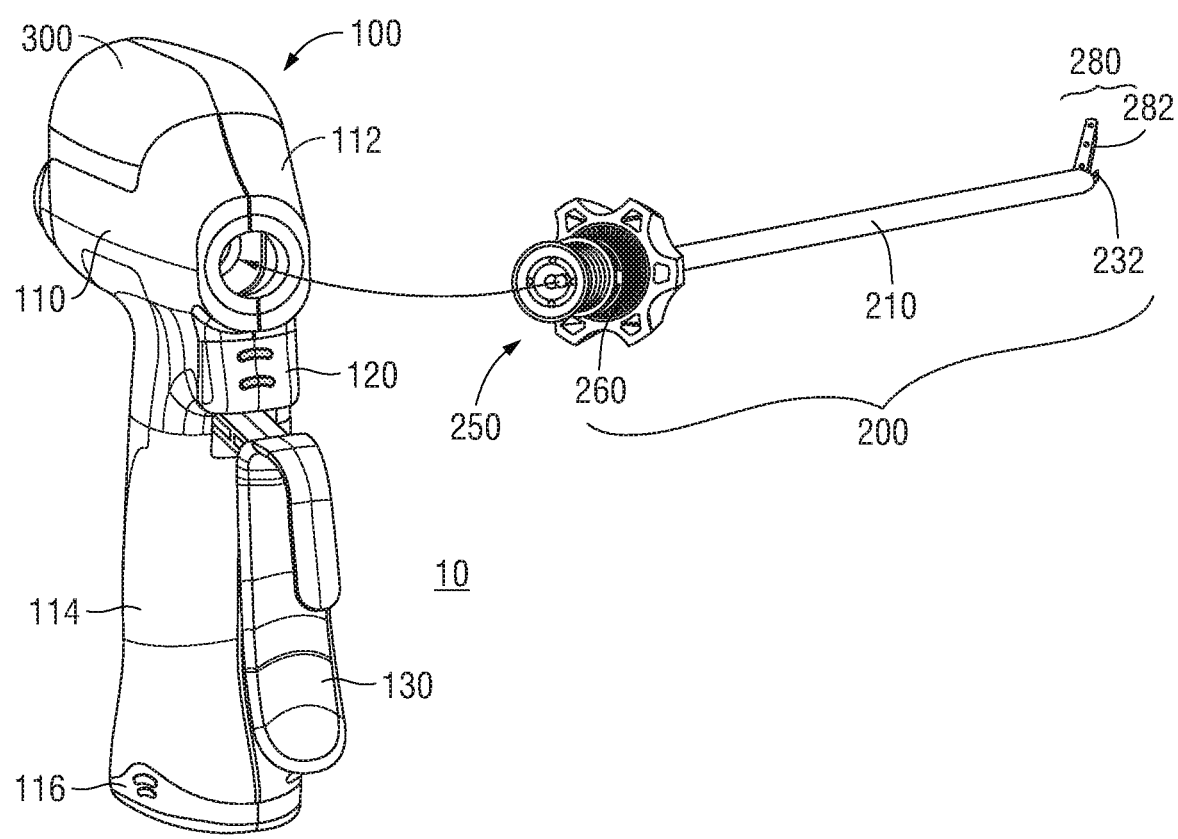
FIG. 2 is a perspective view of the ultrasonic surgical instrument of FIG. 1 with the elongated assembly separated from the handle assembly.

Referring generally to FIGS. 1 and 2, an ultrasonic surgical instrument provided in accordance with the aspects and features of the present disclosure is shown generally identified by reference numeral 10. Although detailed with respect to ultrasonic surgical instrument 10, the aspects and features of the present disclosure are equally applicable for use with any suitable ultrasonic surgical instrument. Thus, ultrasonic surgical instrument 10 is generally described hereinbelow. Additional features of ultrasonic surgical instrument 10, including the assembly and use thereof, are detailed in U.S. Pat. No. 10,368,898, the entire contents of which are hereby incorporated herein by reference.

Figure 4:
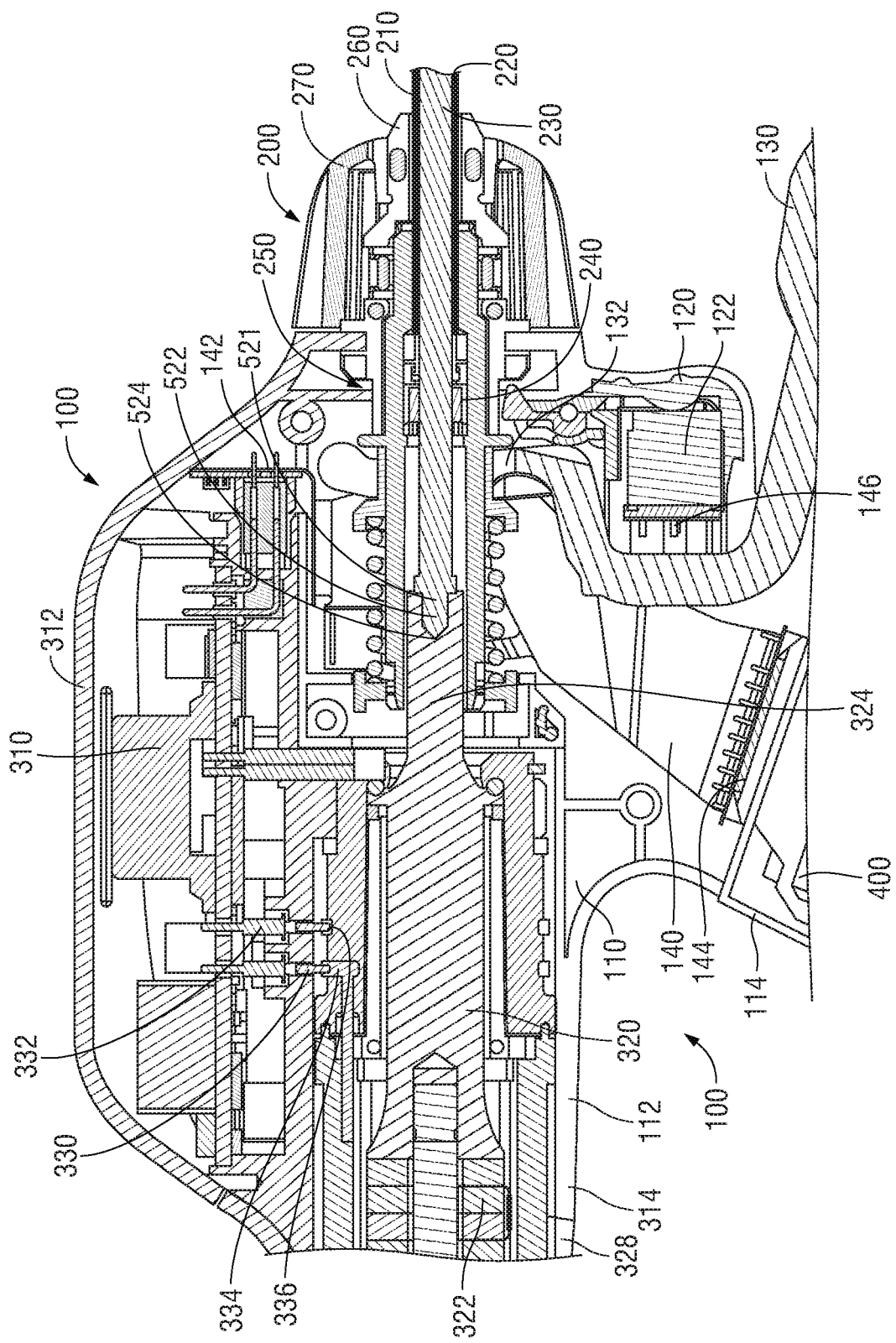
FIG. 4 is an enlarged, longitudinal, cross-sectional view of a portion of the ultrasonic surgical instrument of FIG. 1 illustrating engagement between the elongated assembly and the handle assembly.

Ultrasonic surgical instrument 10 generally includes a handle assembly 100 and an elongated assembly 200 that is configured to releasably engage handle assembly 100. Handle assembly 100 includes a housing 110 defining a body portion 112 configured to support an ultrasonic transducer and generator assembly ("TAG") 300, and a fixed handle portion 114 defining a compartment 116 configured to receive a battery assembly 400 (FIG. 4). Handle assembly 100 further includes an activation button 120 operably positioned to electrically couple between TAG 300 and battery assembly 400 (FIG. 4) when TAG 300 is mounted on body portion 112 of housing 110 and battery assembly 400 (FIG. 4) is engaged within compartment 116 of housing 110.

A clamp trigger 130 extends from housing 110 of handle assembly 100 adjacent to fixed handle portion 114 of housing 110. Clamp trigger 130 includes a bifurcated drive portion 132 extending into body portion 112 of housing 110 and is selectively movable relative to housing 110 to actuate ultrasonic surgical instrument 10.

TAG 300 and battery assembly 400 (FIG. 4), as noted above, are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. Battery assembly 400 (FIG. 4), on the other hand, is configured to be aseptically transferred and retained within compartment 116 of fixed handle portion 114 of housing 110 of handle assembly 100 such that battery assembly 400 (FIG. 4) may be repeatedly used without requiring sterilization thereof.

With additional reference to FIG. 4, an electrical connector 140 disposed within housing 110 of handle assembly 100 includes TAG contacts 142, battery assembly contacts 144, and an activation button connector 146. Electrical connector 140 electrically couples to activation button 120 via activation button connector 146, is configured to electrically couple to TAG 300 via TAG contacts 142 upon engagement of TAG 300 with body portion 112 of housing 110 of handle assembly 100, and is configured to electrically couple to battery assembly 400 via battery assembly contacts 144 upon engagement of battery assembly 400 within compartment 116 of fixed handle portion 114 of housing 110 of handle assembly 100. As such, in use, when activation button 120 is activated in an appropriate manner, an underlying two-mode switch assembly 122 is activated to supply power from battery assembly 400 to TAG 300 in either a "LOW" power mode or a "HIGH" power mode, depending upon the manner of activation of activation button 120.

Continuing with reference to FIGS. 1, 2, and 4, TAG 300 includes a generator 310 and an ultrasonic transducer 320. Generator 310 includes a housing 312 configured to house the internal electronics of generator 310, and a cradle 314 configured to rotatably support ultrasonic transducer 320. Ultrasonic transducer 320 includes a piezoelectric stack 322 and a distally-extending horn 324. A set of connectors 330, 332 and corresponding rotational contacts 334, 336 associated with generator 310 and ultrasonic transducer 320, respectively, enable drive signals to be communicated from generator 310 to piezoelectric stack 322 to drive ultrasonic transducer 320. More specifically, piezoelectric stack 322 of ultrasonic transducer 320 converts a high voltage AC signal received from generator 310 into mechanical motion that is output from horn 324 to elongated assembly 200, as detailed below. Ultrasonic transducer 320 further includes a rotation knob 328 disposed at a proximal end thereof to enable rotation of ultrasonic transducer 320 relative to generator 310.

Figure 3:
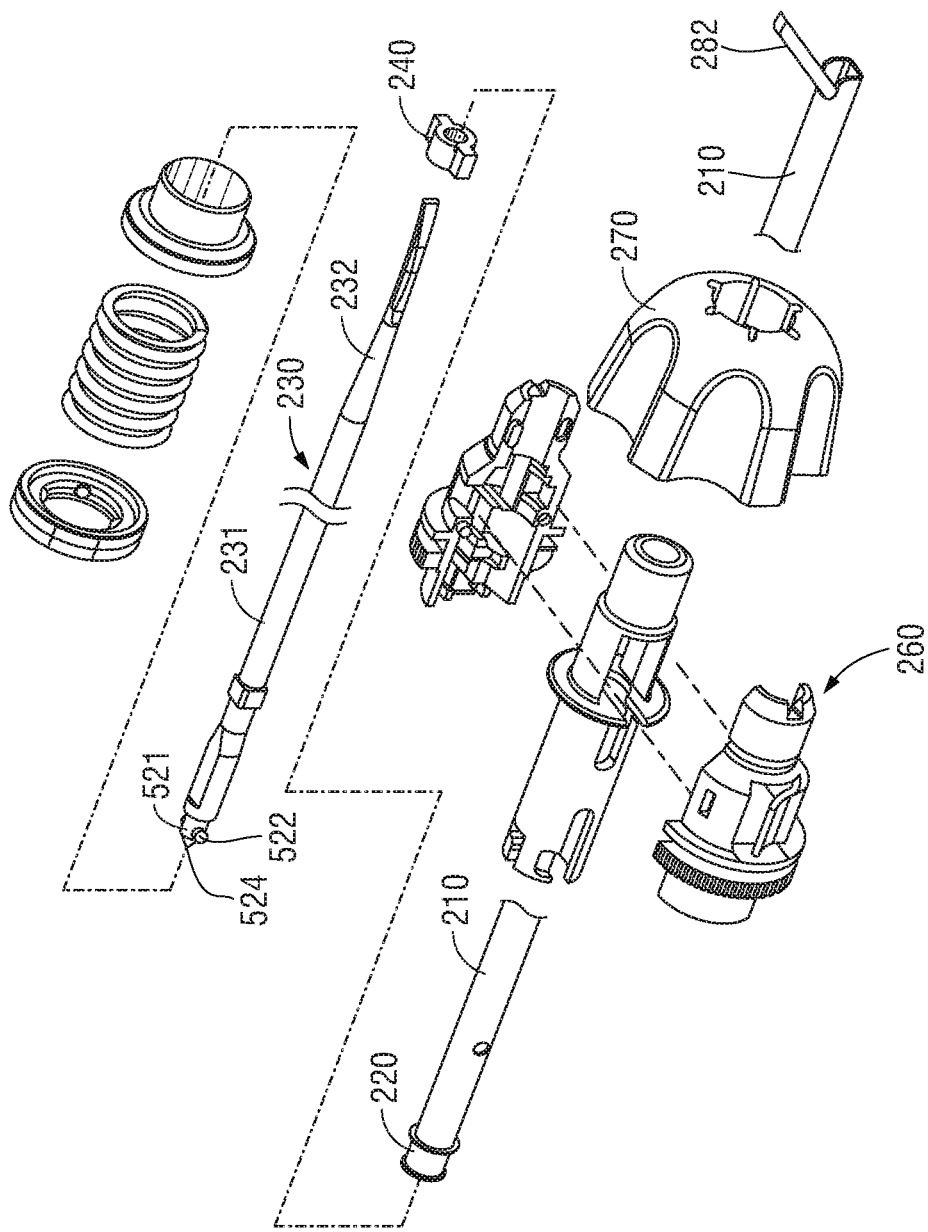
FIG. 3 is an exploded, perspective view of the elongated assembly of FIG. 2.

Referring to FIGS. 2-3, elongated assembly 200 includes an outer drive sleeve 210, an inner support sleeve 220 disposed within outer drive sleeve 210 and about which outer drive sleeve 210 is configured to slide, a waveguide 230 extending through inner support sleeve 220, a torque adapter 240 engaged about waveguide 230, a drive assembly 250 disposed about outer drive sleeve 210 and operably coupled between outer drive sleeve 210 and bifurcated drive portion 132 of clamp trigger 130 (FIG. 4), a torque housing 260 disposed about outer drive sleeve 210 and operably coupled to waveguide 230, a rotation knob 270 operably disposed about torque housing 260, and an end effector 280 (including a jaw member 282) disposed at the distal end of inner support sleeve 220. Waveguide 230 defines the horn 324, a body 231 extending distally from a distal end 324a of the horn 324, and a blade 232 extending distally from a distal end 231b of the body 231. Elongated assembly 200 is configured to releasably engage handle assembly 100 such that mechanical motion output from horn 324 of ultrasonic transducer 320 is transmitted along waveguide 230 to end effector 280 for treating tissue therewith, such that clamp trigger 130 is selectively actuatable to manipulate end effector 280, and such that rotation knob 270 is selectively rotatable to rotate elongated assembly 200 relative to handle assembly 100. Elongated assembly 200 may be configured as a disposable, single-use component or a reusable component that is sterilizable for subsequent use. In embodiments, elongated assembly 200 is integrated with handle assembly 100 and, in such embodiments, is not removable therefrom.

Figure 5:
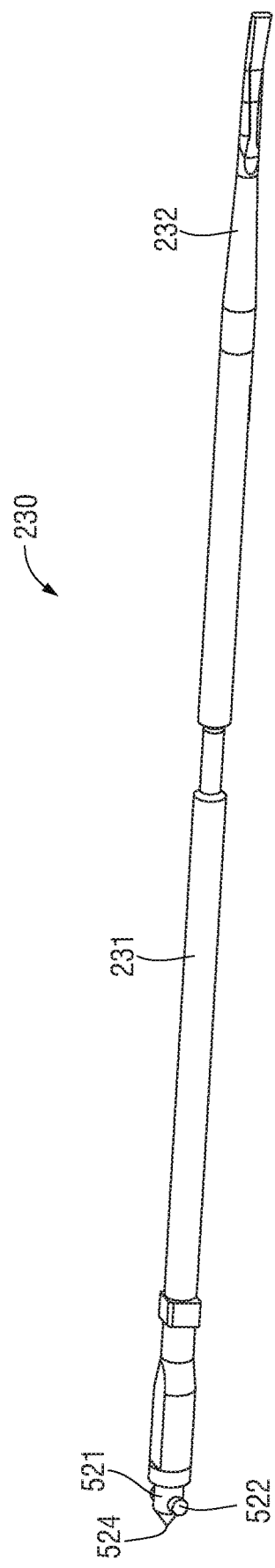
FIG. 5 is a side view of a waveguide in accordance with the present disclosure configured for use with the ultrasonic surgical instrument of FIG. 1.

With additional reference to FIGS. 4-5, waveguide 230, as noted above, extends through inner support sleeve 220. Waveguide 230 defines the horn 324, the body 231, and a blade 232. The body 231 extends distally from the distal end 324a of the horn 324. The blade 232 extends from the distal end 231b of the body 231. Blade 232 extends distally from inner support sleeve 220 and forms part of end effector 280 in that blade 232 is positioned to oppose jaw member 282 such that pivoting of jaw member 282 from the open position to the clamping position enables clamping of tissue between jaw member 282 and blade 232. Blade 232 defines a curved configuration wherein the directions of movement of jaw member 282 between the open and clamping positions are perpendicular to the direction of curvature of blade 232. However, it is also contemplated that blade 232 define a straight configuration or that blade 232 curve towards or away from jaw member 282, that is, where the directions of movement of jaw member 282 between the open and clamping positions are coaxial or parallel to the direction of curvature of blade 232.

Figure 6:
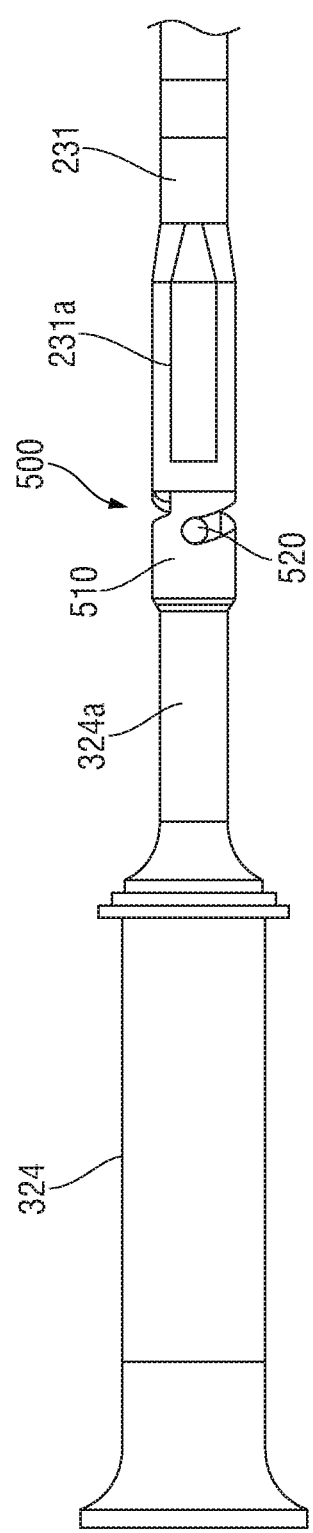
FIG. 6 is a side view of a proximal portion of the waveguide of FIG. 5 illustrating engagement between the horn and the body by a bi-stable spring-latch connector.
Figure 7:
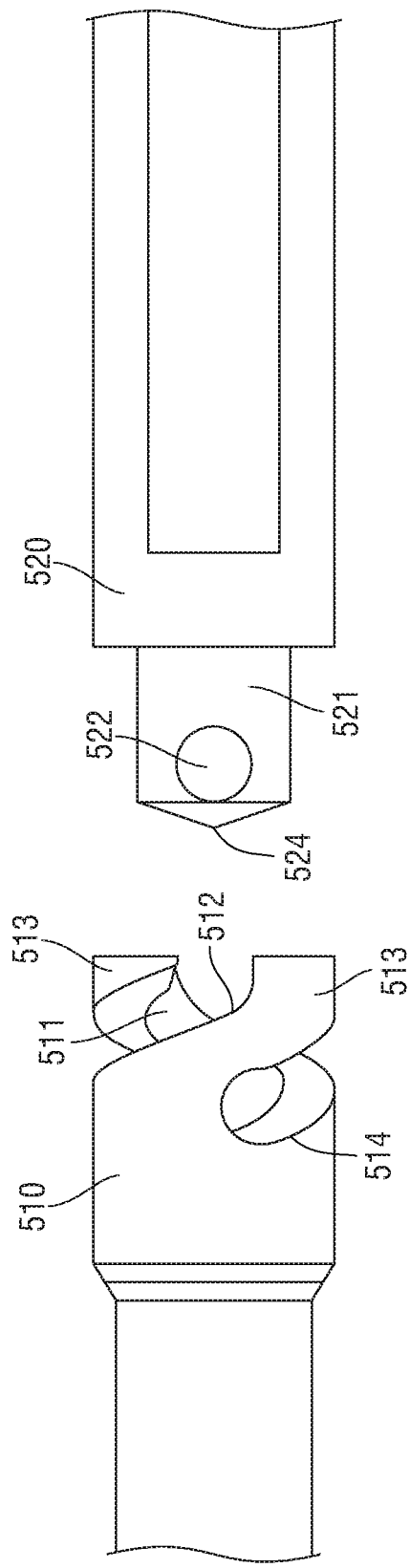
FIG. 7 is an enlarged, side view of the bi-stable spring-latch connector of FIG. 6, in a disengaged condition.
Figure 8:
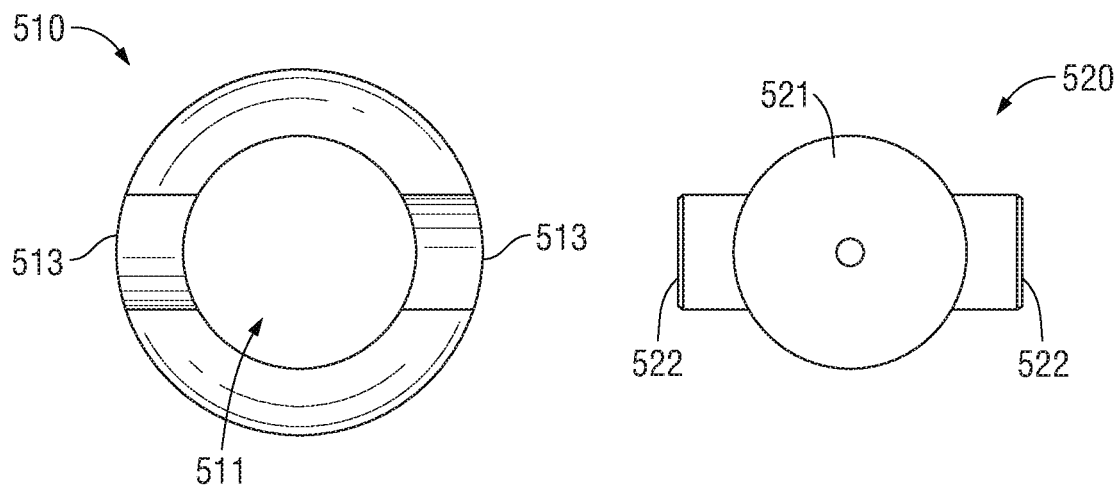
FIG. 8 is an end view illustrating the inside of the female receiving end and the pair of protrusions disposed on the male end of the bi-stable spring-latch connector of FIG. 6.

Referring to FIG. 6-8, a bi-stable spring-latch connector 500 is configured to releasbly couple horn 324 and body 231. The bi-stable spring-latch connector 500 includes a female end 510 and a male end 520. The female end 510 includes an open-ended cylinder 511 with a hollow cylindrical interior 512. The female end 510 further includes a pair of grooves 513 defined within the wall of the open-ended cylinder 511. The grooves 513 are open at the open end of the open-ended cylinder 511 and define a double helix 514.

The male end 520 of the bi-stable spring-latch connector 500 is a cylindrical block 521 having a pair of protrusions 522 disposed on opposite sides of the cylindrical block 521 and extending radially outwardly therefrom. The cylindrical block 521 may have a pointed cap 524, resembling a cone, or other suitable configuration facilitating insertion into the open-ended cylinder 511 of the female end 510. The hollow cylindrical interior 512 of the female end 510 is configured to receive the pointed cap 524 of the cylindrical block 521 of the male end 520. The protrusions 522 disposed on the male end 520 are configured to be inserted through the open ends of the grooves 513 of the female end 510 and, thereafter, the male end 520 is rotated relative to the female end 510 (or vice versa) such that the protrusions 522 are configured to be rotated through the grooves 513 defining the double helix 514 of the female end 510. The protrusions 522 are diametrically opposed on opposite sides of the cylindrical block 521. The pair of protrusions 522 may be substantially round to be easily inserted into and rotated through the double helix 514 of the female end 510, thereby facilitating coupling.

The female end 510 and the male end 520 are coupled through a push and twist motion that is simultaneous, near-simultaneous, consecutive, or otherwise effected. More specifically, the pointed cap 524 of the cylindrical block 521 of the male end 520 is pushed into the hollow cylindrical interior 512 of the female end 510 such that the protrusions 522 disposed on the male end 520 are received within the open ends of the grooves 513. Then, the pair of protrusions 522 disposed on the male end 520 is rotated through the grooves 513, e.g., double helix 514 of the grooves 513, of the female end 510 to couple the female end 510 and the male end 520 via the hollow cylindrical interior 512 and the double helix 514, thereby facilitating a secure connection.

With particular reference to FIG. 6, the female end 510 of the bi-stable spring-latch connector 500 is disposed on a distal end 324a of the horn 324 and the male end 520 of the bi-stable spring-latch connector 500 is disposed on a proximal end 231a of the body 231, although this configuration may be reversed. The grooves 513 defining the double helix 514 are wound, for example, such that clockwise rotation of the male end 520 relative to the female end 510 couples the horn 324 and the body 231 and such that counterclockwise rotation of the male end 520 relative to the female end 510 decouples the horn 324 and the body 231. In other embodiments, the grooves 513 defining the double helix 514 are wound such that counterclockwise rotation couples the horn 324 and the body 231 while clockwise rotation decouples the horn 324 and the body 231.

Figure 9:
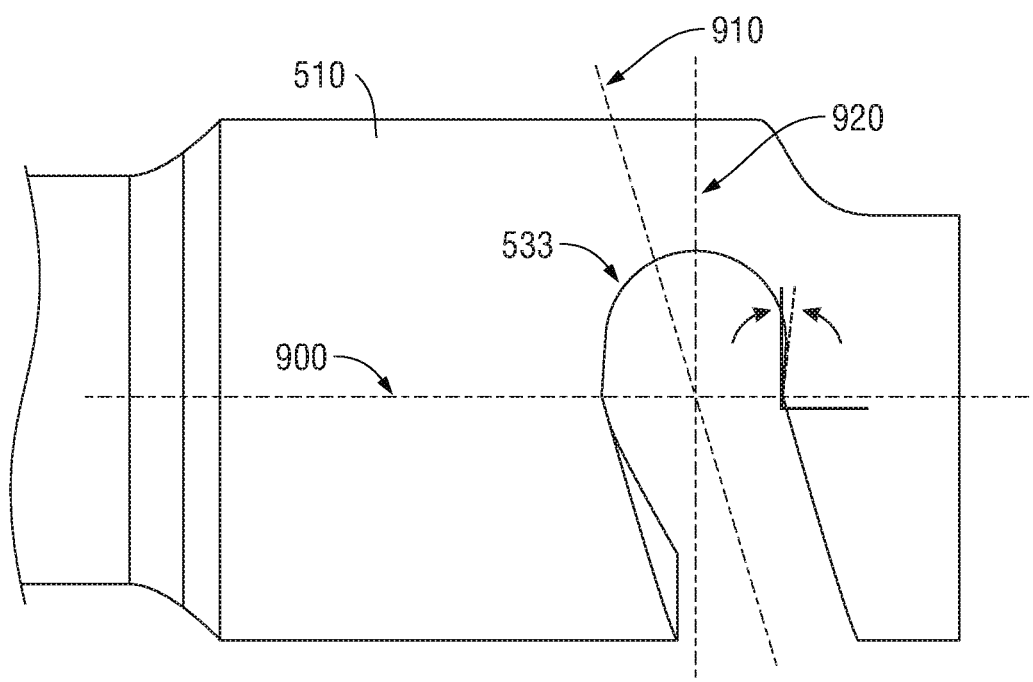
FIG. 9 is an enlarged, side view of the female end of the bi-stable spring-latch connector.

Referring to FIG. 9, closed end segments 533 of the grooves 513 forming the double helix 514 are angled to diverge from a pitch axis 910 of the double helix 514 and extend perpendicular to a longitudinal axis 900 defined through the female end 510. Additionally, there is a closed distal segment axis 920. By angling off the pitch axis 910 of the double helix 514, the closed end segments 533 of grooves 513 forming the double helix 514 are positioned such that when the protrusions 522 are received within the closed end segments 533, the coupling of the female end 510 and the male end 520 is maintained under compression. This compression is configured to limit the loss when ultrasonic vibrations are transmitted along the waveguide. As described above, the pair of protrusions 522 may be substantially round to be easily rotated through the double helix 514 of the female end 510, thereby facilitating coupling. The closed end segments 533 of the double helix 514, being perpendicular to the longitudinal axis 900, configure the pair of protrusions 522 of the male end 520 to lock into place with the closed end segments 533 of the double helix 514.

In some embodiments, horn 324 and body 231 may be coupled via a threaded connection. The horn 324 may define a threaded female receiver at a distal end thereof. A threaded male shaft on a proximal end 231a of the body 231 may be configured for threaded engagement with the threaded female receiver of horn 324. In other embodiments a threaded female receiver is disposed on proximal end of body 231 configured to receive a threaded male shaft from distal end of horn 324.

In some embodiments, horn 324 and body 231 may be formed from a single, monolithic piece or may otherwise be formed as a unitary structure. Body 231 may be injection molded to solidify and define an interference fit bonding 235 between horn 324 and body 231, using titanium or titanium alloys to form body 231.

Figure 10:
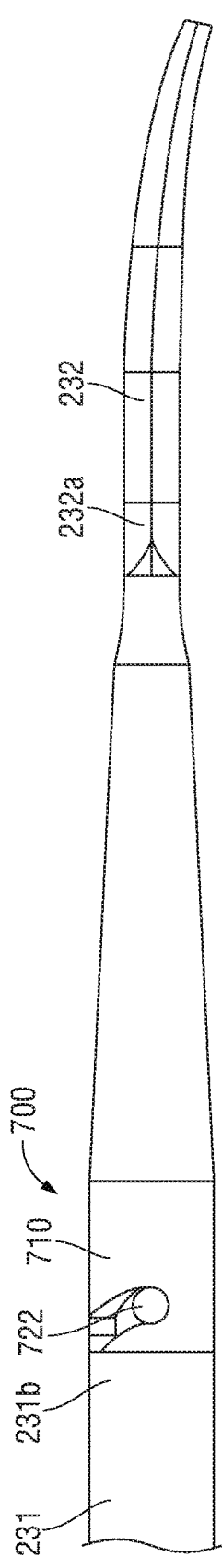
FIG. 10 is a side view of a distal portion of the waveguide of FIG. 5 illustrating engagement between the body and the blade by a bi-stable spring-latch connector.

Referring to FIG. 10, blade 232 is fixedly engaged to a distal end of the body 231b. Blade 232 extends distally from the distal end of the body 231b and is configured to receive ultrasonic energy from the body 231 for treating tissue in contact with blade 232, e.g., clamped between blade 232 and jaw member 282 (FIG. 1). In some embodiments, body 231 is formed from titanium or a titanium alloy, and blade 232 is formed from an amorphous material.

In some embodiments, blade 232 is injection molded to solidify and define an interference fit bonding 235 between body 231 and blade 232. The injection molding process allows for blade 232 to be formed from amorphous materials, e.g., metallic amorphous materials or metallic glass amorphous materials, that have higher material strength properties than the titanium or titanium alloys that are used to form body 231. The injection molding process also avoids the added manufacturing cost of machining intricate features onto blade 232.

Figure 11:
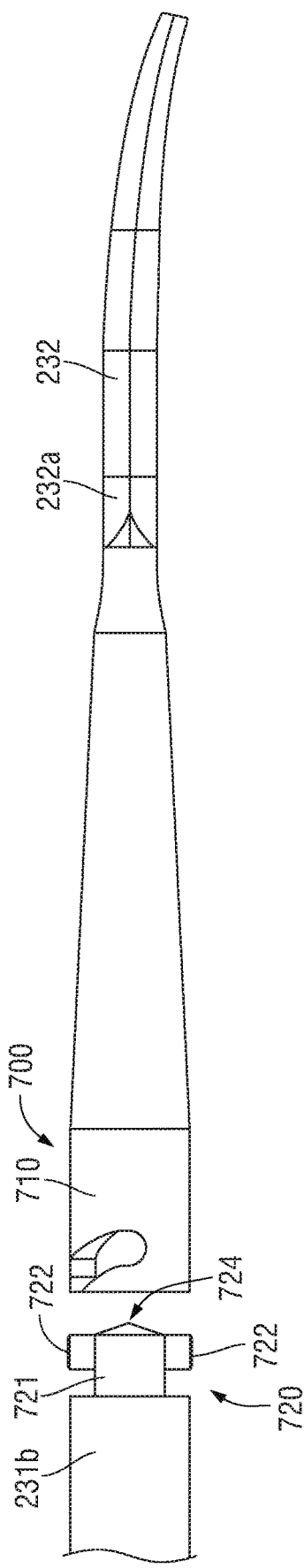
FIG. 11 is an enlarged, side view of the bi-stable spring-latch connector of FIG. 10, in a disengaged condition.
Figure 12:
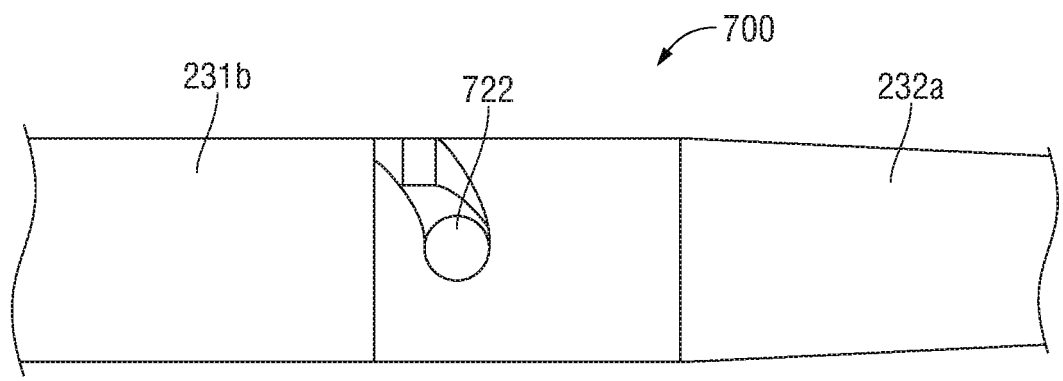
FIG. 12 is an enlarged, side view of the bi-stable spring-latch connector of FIG. 11, in an engaged condition.

With reference to FIGS. 10-12, a bi-stable spring-latch connector 700 is configured to releasbly couple a body 231 and a blade 232. This bi-stable spring-latch connector 700 comprises a male end 720 and a female end 710.

The female end 710 includes an open-ended cylinder 711 with a hollow cylindrical interior 712. The female end 710 further includes a pair of grooves 713 defined within the wall of the open-ended cylinder 711. The grooves 713 are open at the open end of the open-ended cylinder 711 and define a double helix 714.

The male end 720 of the bi-stable spring-latch connector 700 is a cylindrical block 721 having a pair of protrusions 722 disposed on opposite sides of the cylindrical block 721 and extending radially outwardly therefrom. The cylindrical block 721 may have a pointed cap 724, resembling a cone, or other suitable configuration facilitating insertion into the open-ended cylinder 711 of the female end 710. The hollow cylindrical interior 712 of the female end 710 is configured to receive the pointed cap 724 of the cylindrical block 721 of the male end 720. The protrusions 722 disposed on the male end 720 are configured to be inserted through the open ends of the grooves 713 of the female end 710 and, thereafter, the male end 720 is rotated relative to the female end 710 (or vice versa) such that the protrusions 722 are configured to be rotated through the grooves 713 defining the double helix 714 of the female end 710. The protrusions 722 are diametrically opposed on opposite sides of the cylindrical block 721. The pair of protrusions 722 may be substantially round to be easily inserted into and rotated through the double helix 714 of the female end 510, thereby facilitating coupling.

The female end 710 and the male end 720 are coupled through a push and twist motion that is simultaneous, near-simultaneous, consecutive, or otherwise effected. More specifically, the pointed cap 724 of the cylindrical block 721 of the male end 720 is pushed into the hollow cylindrical interior 712 of the female end 710 such that the protrusions 722 disposed on the male end 720 are received within the open ends for the grooves 713. Then, the pair of protrusions 722 disposed on the male end 720 is rotated through the grooves 713, e.g., double helix 714 of the grooves 713, of the female end 710 to couple the female end 710 and the male end 720 via the hollow cylindrical interior 712 and the double helix 714, thereby facilitating a secure connection.

With particular reference to FIG. 10, the female end 710 of the bi-stable spring-latch connector 700 is disposed on a distal end 231b of the body 231 and the male end 720 of the bi-stable spring-latch connector 700 is disposed on a proximal end 232a of the blade 232, although this configuration may be reversed. The grooves 713 defining the double helix 714, in embodiments, are wound such that clockwise rotation of the male end 720 relative to the female end 710 couples the body 231 and the blade 232 and such that counterclockwise rotation of the male end 720 relative to the female end 710 decouples the body 231 and the blade 232, although the opposite configuration is also contemplated.

In some embodiments, waveguide 230, defining a horn 324, a body 231, and a blade 232, may include a plurality of bi-stable spring-latch connectors. In this embodiment, bi-stable spring-latch connector 500 may be used to couple the horn 324 and the body 231, and bi-stable spring-latch connector 700 may be used to couple the body 231 and the blade 232. Further, rather than just connecting a horn, a body, and/or a blade with one another, the bi-stable spring-latch connectors of the present disclosure may also be utilized to couple different waveguide, ultrasonic system, or other components with one another to provide a releasable bi-stable spring-latch connection.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A waveguide configured for use with an ultrasonic surgical instrument, the waveguide comprising:
   a horn configured to receive ultrasonic energy from an ultrasonic transducer, the horn including a distal end portion;
   a body including a proximal end portion, the body extending distally from the horn and configured to transmit the ultrasonic energy therealong;
   a blade extending distally from the body and configured to apply the ultrasonic energy to tissue in contact therewith to treat the tissue; and
   a bi-stable spring-latch connector releasably coupling, under an end compression, the horn and the body, the bi-stable spring-latch connector including at least one protrusion disposed on one of the distal end portion of the horn or the proximal end portion of the body and at least one helical groove defined within the other of the distal end portion of the horn or the proximal end portion of the body, the at least one helical groove having an open end portion and extending away from the one of the distal end portion of the horn or the proximal end portion of the body from the open end portion to a closed end portion of the at least one helical groove such that relative rotation between the horn and the body moves the at least one protrusion through the at least one helical groove from the open end portion towards the closed end portion to thereby urge the horn and the body towards one another and increasingly compress the distal end portion of the horn and the proximal end portion of the body against one another until the end compression is achieved when the at least one protrusion reaches the closed end portion of the at least one helical groove.

2. The waveguide according to claim 1, wherein the bi-stable spring-latch connector comprises a female end disposed on the distal end portion of the horn and a male end disposed on the proximal end portion of the body, the female end configured to receive the male end thereby releasably coupling, under the end compression, the horn and the body.

3. The waveguide according to claim 2, wherein the female end of the bi-stable spring-latch connector is an open-ended cylinder with a hollow cylindrical interior and the at least one helical groove, wherein the at least one helical groove includes a pair of helical grooves defining a double helix.

4. The waveguide according to claim 3, wherein the male end of the bi-stable spring-latch connector is a cylindrical block having the at least one protrusion, wherein the at least one protrusion includes a pair of protrusions disposed on opposite sides of the cylindrical block and extending radially outwardly therefrom.

5. The waveguide according to claim 4, wherein the pair of protrusions disposed on the male end is configured to be rotated through the double helix of the female end.

6. The waveguide according to claim 5, wherein the closed end portions ends of the helical grooves of the double helix are perpendicular to a longitudinal axis defined through the female end, thereby maintaining the coupling, under the end compression, of the female end and the male end.

7. The waveguide according to claim 6, wherein the helical grooves of the double helix are wound clockwise such that clockwise rotation of the male end relative to the female end couples the horn and the body.

8. The waveguide according to claim 6, wherein the helical grooves of the double helix are wound counterclockwise such that counterclockwise rotation of the male end relative to the female end couples the horn and the body.

9. The waveguide according to claim 1, wherein the bi-stable spring-latch connector comprises a male end disposed on a distal end portion of the horn and a female end disposed on a proximal end portion of the body, the female end configured to receive the male end thereby releasably coupling, under the end compression, the horn and the body.

10. A waveguide configured for use with an ultrasonic surgical instrument, the waveguide comprising:
a horn configured to receive ultrasonic energy from an ultrasonic transducer;
a body extending distally from the horn and configured to transmit the ultrasonic energy therealong, the body defining a distal end portion;
a blade extending distally from the body and configured to apply the ultrasonic energy to tissue in contact therewith to treat the tissue, the blade defining a proximal end portion; and
a bi-stable spring-latch connector releasably coupling, under an end compression, the body and the blade, the bi-stable spring-latch connector including at least one protrusion disposed on one of the distal end portion of the body or the proximal end portion of the blade and at least one helical groove defined within the other of the distal end portion of the body or the proximal end portion of the blade, the at least one helical groove having an open end portion and extending away from the one of the distal end portion of the body or the proximal end portion of the blade from the open end portion to a closed end portion of the at least one helical groove such that relative rotation between the body and the blade moves the at least one protrusion through the at least one helical groove from the open end portion towards the closed end portion to thereby urge the body and the blade towards one another and increasingly compress the distal end portion of the body and the proximal end portion of the blade against one another until the end compression is achieved when the at least one protrusion reaches the closed end portion of the at least one helical groove.

11. The waveguide according to claim 10, wherein the bi-stable spring-latch connector comprises a female end disposed on the distal end portion of the body and a male end disposed on the proximal end portion of the blade, the female end configured to receive the male end thereby releasably coupling, under the end compression, the body and the blade.

12. The waveguide according to claim 11, wherein the female end of the bi-stable spring-latch connector is an open-ended cylinder with a hollow cylindrical interior and the at least one helical groove, wherein the at least one helical groove includes a pair of helical grooves defining a double helix.

13. The waveguide according to claim 12, wherein the male end of the bi-stable spring-latch connector is a cylindrical block having the at least one protrusion, wherein the at least one protrusion includes a pair of protrusions disposed on opposite sides of the cylindrical block and extending radially outwardly therefrom.

14. The waveguide according to claim 13, wherein the pair of protrusions disposed on the male end is configured to be rotated through the double helix of the female end.

15. The waveguide according to claim 14, wherein the closed end portions of the helical grooves of the double helix are perpendicular to a longitudinal axis defined through the female end, thereby maintaining the coupling, under the end compression, of the female end and the male end.

16. The waveguide according to claim 15, wherein the helical grooves of the double helix are wound clockwise such that clockwise rotation of the male end relative to the female end couples the body and the blade.

17. The waveguide according to claim 15, wherein the helical grooves of the double helix are wound counterclockwise such that counterclockwise rotation of the male end relative to the female end couples the body and the blade.

18. The waveguide according to claim 10, wherein the bi-stable spring-latch connector comprises a male end disposed on the distal end portion of the body and a female end disposed on the proximal end portion of the blade, the female end configured to receive the male end thereby releasably coupling, under the end compression, the body and the blade.

* * * * *